United States Patent [19]

Ramsey, III et al.

[11] Patent Number: 5,606,977
[45] Date of Patent: Mar. 4, 1997

[54] OSCILLOMETRIC BLOOD PRESSURE MONITOR WHICH AUTOMATICALLY DETERMINES WHEN TO TAKE BLOOD PRESSURE MEASUREMENTS

[75] Inventors: Maynard Ramsey, III; Richard Medero, both of Tampa, Fla.

[73] Assignee: Critikon, Inc., Tampa, Fla.

[21] Appl. No.: 368,425

[22] Filed: Jan. 4, 1995

[51] Int. Cl.$^6$ .......................................... A61B 5/00
[52] U.S. Cl. ........................ 128/680; 128/681; 128/682; 128/687
[58] Field of Search ................ 128/677, 680–683, 128/687, 672

[56] References Cited

U.S. PATENT DOCUMENTS

| | | | |
|---|---|---|---|
| 4,349,034 | 9/1982 | Ramsey, III | 128/681 |
| 4,360,029 | 11/1982 | Ramsey, III | 128/681 |
| 4,461,266 | 7/1984 | Hood, Jr. et al. | 128/681 |
| 4,543,962 | 10/1985 | Medero et al. | 128/682 |
| 4,546,775 | 10/1985 | Medero | 128/681 |
| 4,627,440 | 12/1986 | Ramsey, III et al. | 128/682 |
| 4,638,810 | 1/1987 | Ramsey, III et al. | 128/681 |
| 4,664,126 | 5/1987 | Link | 128/680 |
| 4,669,485 | 6/1987 | Russell | 128/681 |
| 4,754,761 | 7/1988 | Ramsey, III et al. | 128/683 |
| 4,774,960 | 10/1988 | Arnold et al. | 128/681 |
| 4,850,368 | 1/1989 | Miyawaki | 128/680 |
| 4,889,133 | 12/1989 | Nelson et al. | 128/681 |
| 4,926,873 | 5/1990 | Frankenreiter | 128/681 |
| 4,949,710 | 8/1990 | Dorsett et al. | 128/680 |
| 4,984,577 | 1/1991 | Frankenreiter | 128/681 |
| 5,052,397 | 10/1991 | Ramsey, III et al. | 128/682 |
| 5,054,495 | 10/1991 | Uemura et al. | 128/680 |
| 5,103,833 | 4/1992 | Apple | 128/687 |
| 5,170,795 | 12/1992 | Ramsey, III et al. | 128/682 |
| 5,218,967 | 6/1993 | Apple | 128/687 |
| 5,253,648 | 10/1993 | Walloch | 128/681 |
| 5,261,413 | 11/1993 | Kawahara | 128/682 |
| 5,279,303 | 1/1994 | Kawamura et al. | 128/687 |
| 5,280,790 | 1/1994 | Brooks | 128/681 |
| 5,311,872 | 5/1994 | Apple | 128/687 |

FOREIGN PATENT DOCUMENTS

| | | |
|---|---|---|
| 0655219A1 | 5/1995 | European Pat. Off. . |
| 0698370A2 | 2/1996 | European Pat. Off. . |

*Primary Examiner*—Angela D. Sykes
*Assistant Examiner*—Robert L. Nasser, Jr.
*Attorney, Agent, or Firm*—Woodcock Washburn Kurtz Mackiewicz & Norris

[57] ABSTRACT

An automated sphygmomanometer which automatically determines when a blood pressure determination needs to be made. During a "guard mode" determination, a cuff on an appendage of the patient is frequently inflated to a check pressure, which is preferably below the patient's mean arterial pressure ("MAP"), and the signature (shape, amplitude, pulse period, etc.) of the measured oscillometric signal is compared to a stored signature of a portion of an oscillometric signal at a corresponding portion of the oscillometric envelope determined during a previous blood pressure determination. If these signals differ by some predetermined amount, it is determined that the patient's blood pressure has changed significantly and that a new blood pressure determination needs to be conducted immediately. These guard mode determinations are made in addition to the normal blood pressure determinations made at predetermined intervals typically selected by the user. In addition, the shape of the oscillometric signal is quantified during guard mode so that it is possible to discriminate oscillations on the diastolic side of a patient's oscillometric envelope from oscillations on the systolic side of the patient's oscillometric envelope, thereby preventing a large shift in the oscillometric envelope from going undetected.

17 Claims, 4 Drawing Sheets

OSCILLOMETRIC BLOOD PRESSURE MONITOR WHICH AUTOMATICALLY DETERMINES WHEN TO TAKE BLOOD PRESSURE MEASUREMENTS

FIELD OF THE INVENTION

This invention relates to automated blood pressure monitoring, and more particularly, to automated blood pressure monitors that utilize a pneumatic cuff for accomplishing a sphygmomanometric measurement on a patient.

BACKGROUND OF THE INVENTION

The sphygmomanometric class of automated blood pressure monitors employs an inflatable cuff to exert controlled counter-pressure on the vasculature of a patient. One large class of such monitors, exemplified by that described in U.S. Pat. Nos. 4,349,034 and 4,360,029, both to Maynard Ramsey, III and commonly assigned herewith, employs the oscillometric methodology. In accordance with the Ramsey patents, an inflatable cuff is suitably located on the limb of a patient and is pumped up to a predetermined pressure above the systolic pressure. Then, the cuff pressure is reduced in predetermined decrements, and at each level, pressure fluctuations are monitored. The resultant signals typically consist of a DC voltage with a small superimposed variational component caused by arterial blood pressure pulsations (referred to herein as "oscillation complexes" or just simply "oscillations"). After suitable filtering to reject the DC component and to provide amplification, peak pulse amplitudes (PPA) above a given base-line are measured and stored. As the decrementing continues, the peak amplitudes will normally increase from a lower level to a relative maximum, and thereafter will decrease. These amplitudes thus form an oscillometric blood pressure envelope for the patient. The lowest cuff pressure at which the oscillations have a maximum value has been found to be representative of the mean arterial pressure ("MAP"). Systolic and diastolic pressures can be derived either as predetermined fractions of MAP, or by more sophisticated methods of direct processing of the oscillation complexes.

The step deflation technique as set forth in the Ramsey patents is the commercial standard of operation. A large percentage of clinically acceptable automated blood pressure monitors utilize the step deflation rationale. When in use, the blood pressure cuff is placed on the patient and the operator sets a time interval, typically from 1 to 90 minutes, at which blood pressure measurements are to be made. The noninvasive blood pressure ("NIBP") monitor automatically starts a blood pressure determination at the end of the set time interval. Typically, the user selects a short interval if the patient is unstable since blood pressure may change to dangerous levels in a short time and selects a longer interval as the patient becomes more stable. The reason a short interval is not used in all cases is that the probability of trauma to the limb from the cuff inflation increases as the determination frequency increases.

Unfortunately, setting the interval for blood pressure measurement is not an exact science. If it is wrongly assumed that the patient's blood pressure is stable and a long interval is set, critical minutes may pass before dangerous changes in pressure are detected. Conversely, if it is wrongly assumed that the patient's blood pressure is volatile, the patient's limb is subjected to many unnecessary cuff inflations and the possible trauma resulting from such cuff inflations.

It is, accordingly, a primary object of the present invention to automatically determine when a blood pressure determination should be made without completely inflating the cuff and possibly causing trauma to the patient.

It is a further object of the present invention to automatically determine whether the patient's blood pressure has changed significantly since the last determination so that a new blood pressure determination may be instigated immediately.

It is also an object of the present invention to provide a technique for monitoring the status of the patient's blood pressure between determinations so that a change in status between blood pressure determinations will not go undetected.

If is a further object of the present invention to provide a technique for monitoring the status of the patient's blood pressure so that full blood pressure determinations need not be taken as frequently, thereby minimizing the possibility of trauma to the patient.

SUMMARY OF THE INVENTION

The above objects have been met in accordance with the present invention by providing an automated sphygmomanometer which frequently inflates to a check pressure below the mean arterial pressure ("MAP") and compares the detected oscillometric signal at the check pressure on the oscillometric envelope to a stored oscillometric signal at the corresponding pressure on the oscillometric envelope of a previous blood pressure determination. Preferably, the check pressure is diastolic pressure. In other words, "snapshot" signals at certain points on the patient's oscillometric envelope are compared, and if they differ by a predetermined amount, it is determined that the patient's blood pressure has changed significantly and that a new blood pressure determination should be initiated immediately (i.e., before the expiration of a user set time interval). For example, a check inflate to a pressure below MAP for a "snapshot" pressure determination may be conducted at a cycle time which is $\frac{1}{5}$ that of the set time period. These check inflates are performed in addition to the normal determinations that occur at the end of the set time periods.

In accordance with the invention, parameters are stored which identify the oscillometric signal around diastolic pressure, for example. Preferably, the parameters stored during a regular blood pressure determination include envelope (shape and size), diastolic pressure, oscillation shape at diastolic, and pulse period. For the check inflate measurement in accordance with the invention, the same parameters are stored regarding the patient's current condition except for the envelope parameter. The parameters measured during each check inflate are compared with corresponding stored parameters to determine if any particular parameter has changed significantly (say 20% or more) or whether the sum of the deviations of the shape, amplitude and pulse periods has changed significantly (say 30% or more). If so, a normal blood pressure determination is made immediately for a determination of the new MAP. Otherwise, further check inflates are performed until the set time period expires or it is otherwise determined that a complete inflate cycle should be conducted.

The above determinations may be accomplished using just the oscillation amplitudes as the oscillometric envelope parameters. Indeed, the present inventors have observed that amplitude is most sensitive to changes in blood pressure and is most sensitive around diastolic pressure, where the slope of the oscillometric envelope is the greatest. However, if the blood pressure rises enough to shift the oscillometric envelope such that the sample at the old diastolic level is now at about the systolic level, the amplitudes may be similar. It is thus desirable to utilize the afore-mentioned shape parameter to avoid this problem.

The shape parameter is computed in a preferred embodiment by drawing a line from the start of one oscillation to the start of the next oscillation. Another line is drawn from the peak of the first oscillation down to the time axis so as to intersect the line connecting the beginning of the oscillations. Another line is drawn from the peak of the first oscillation to the start of the next oscillation. This line completes a triangle that is on the diastolic phase of the oscillation. The ratio of the area of this triangle and the area under the oscillometric envelope that is between the peak of the first oscillation, the start of the next oscillation, and above the line between the beginning of the oscillations is then calculated. The present inventors have found experimentally that such a ratio for the diastolic part is less than one for oscillation complexes at cuff pressures greater than MAP (systolic phase of the oscillometric envelope) and greater than one for oscillation complexes at cuff pressures less than MAP (diastolic phase of the oscillometric envelope). Accordingly, the ratio can be used to distinguish amplitudes measured on the diastolic and systolic sides of the oscillometric envelope.

By inflating to a level below MAP and maintaining the pressure for only a few pulses, little trauma is caused to the patient's limb as compared to a normal determination that must inflate the cuff above systolic pressure and slowly deflate to a level below diastolic pressure. The present invention thus allows users to select an interval much greater than they now use for respective blood pressure measurements, thereby reducing risk and discomfort to the patient.

BRIEF DESCRIPTION OF THE DRAWINGS

The present invention will be better understood after reading the following detailed description of the presently preferred embodiments thereof with reference to the appended drawings, in which.

DETAILED DESCRIPTION OF THE PRESENTLY PREFERRED EMBODIMENT

A system and method which meets the above-mentioned objects and provides other beneficial features in accordance with the presently preferred exemplary embodiment of the invention will be described below with reference to FIGS. 1–4. Those skilled in the art will readily appreciate that the description given herein with respect to those figures is for explanatory purposes only and is not intended in any way to limit the scope of the invention. Accordingly, all questions regarding the scope of the invention should be resolved by referring to the appended claims.

In U.S. Pat. No. 4,360,029, Ramsey discloses in great detail a system for oscillometric blood pressure monitoring to which the principles of the present invention may be applied with advantage. The disclosure of the commonly assigned Ramsey '029 patent is incorporated by reference herein. The following description of FIG. 1 will act as a brief summary of the operation of that system.

Figure 1:
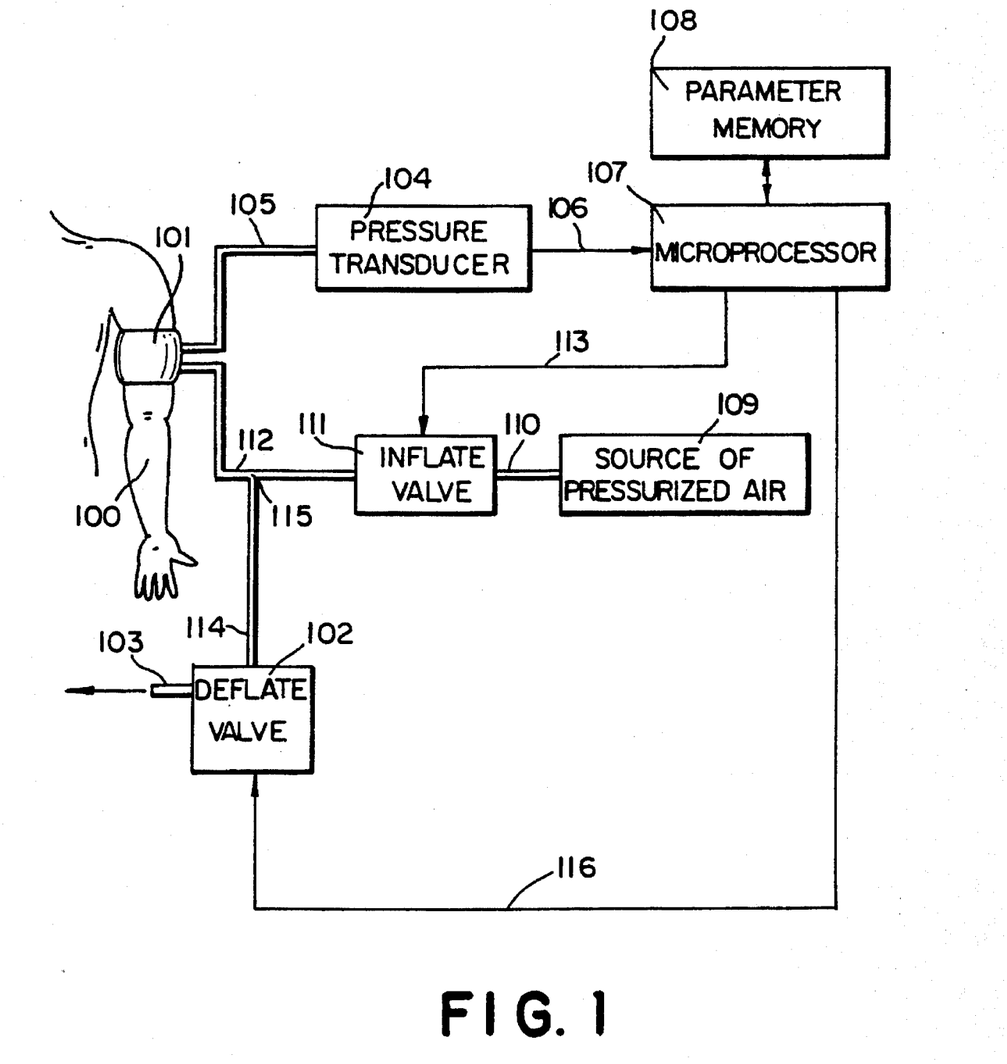
FIG. 1 is a schematic representation of a noninvasive blood pressure ("NIBP") monitor embodying the present invention.

In FIG. 1, the arm 100 of a human subject is shown wearing a conventional flexible inflatable and deflatable cuff 101 for occluding the brachial artery when fully inflated. As the cuff 101 is deflated using deflate valve 102 having exhaust 103, the arterial occlusion is gradually relieved. As will be described more fully below, the deflation of cuff 101 via deflate valve 102 is controlled by microprocessor 107 via control line 116.

A pressure transducer 104 is coupled by a duct 105 to the cuff 101 for sensing the pressure therein. In accordance with conventional oscillometric techniques, pressure oscillations in the artery are sensed by changes in the counter-pressure of the cuff 101, and these pressure oscillations are converted into an electrical signal by transducer 104 and coupled over path 106 to microprocessor 107 for processing. In addition, a source of pressurized air 109 is connected via a duct 110 through an inflate valve 111 and a duct 112 to the pressure cuff 101. The inflate valve 111 is electrically controlled through a connection 113 from the microprocessor 107. Also, the deflate valve 102 is connected by duct 114 via a branch connection 115 with the duct 112 leading to cuff 101. As will be explained more fully below, a parameter memory 108 is also provided for storing parameters such as envelope shape and size, diastolic pressure, oscillation shape at diastolic, and the pulse period representative of the information gathered during each NIBP determination.

From the standpoint of the principles of the present invention, the processing of the signals from pressure transducer 104 by the microprocessor 107 to produce blood pressure data, and optionally to reject artifact data, can be conducted in accordance with the prior art teachings of the above-referenced Ramsey '029 and '034 patents. Alternatively, the blood pressure can be determined in accordance with the teachings of Medero et al. in U.S. Pat. No. 4,543, 962, of Medero in U.S. Pat. No. 4,546,775, of Hood, Jr. et al. in U.S. Pat. No. 4,461,266, of Ramsey, III et al. in U.S. Pat. No. 4,638,810, of Ramsey, III et al. in U.S. Pat. No. 4,754,761, of Ramsey, III et al. in U.S. Pat. No. 5,170,795, and of Ramsey, III et al. in U.S. Pat. No. 5,052,397, all of which are commonly assigned herewith and the disclosures of which are hereby incorporated by reference. In any event, it is desirable to use any of the known techniques to determine the quality of the oscillation complexes received at each level so that the blood pressure determination is made using actual blood pressure data and not artifacts.

The apparatus described above with reference to FIG. 1, except for the programming of the microprocessor 107, can be substantially the same as that disclosed in the Ramsey, III et al. '029 and '034 patents. Thus, during operation of the apparatus illustrated in FIG. 1, it can be assumed that air under pressure to about 8–10 p.s.i. is available in the source of pressurized air 109. When it is desired to initiate a determination of blood pressure, the microprocessor 107 furnishes a signal over path 113 to open the inflate valve 111. The deflate valve 102 is closed. Air from the source 109 is communicated through inflate valve 111 and duct 112 to inflate the cuff 101 to a desired level, preferably above the estimated systolic pressure of the patient. Microprocessor 107 responds to a signal on path 106 from the pressure transducer 104, which is indicative of the instantaneous pressure in the cuff 101, to interrupt the inflation of the cuff 101 when the pressure in the cuff 101 reaches a predetermined value above the estimated systolic pressure of the patient. Such interruption is accomplished by sending a signal over path 113 instructing inflate valve 111 to close. Once inflate valve 111 has been closed, the blood pressure measurement can be obtained by commencing the deflate routine.

As noted above, actual measurement of the blood pressure under the control of the microprocessor 107 and the deflate valve 102 as sensed by pressure transducer 104 can be accomplished in any suitable manner such as that disclosed in the aforementioned patents. At the completion of each measurement cycle, the deflate valve 102 can be reopened long enough to relax the cuff pressure substantially completely via exhaust 103. Thereafter, the deflate valve 102 is closed for the start of a new measurement cycle.

By way of a summation, when a blood pressure measurement is desired, the inflate valve 111 is opened while the cuff pressure is supervised by pressure transducer 104 until the cuff pressure reaches the desired level. The inflate valve 111 is then closed. Thereafter, the deflate valve 102 is operated using signal 116 from microprocessor 107 and the blood pressure measurement taken. To this point, the monitor operates in a conventional manner. The present invention relates to a technique which automatically starts the above-described measurement process when it is determined that the patient's blood pressure may have changed, even though the set interval for NIBP determinations has not yet expired.

Figure 2:
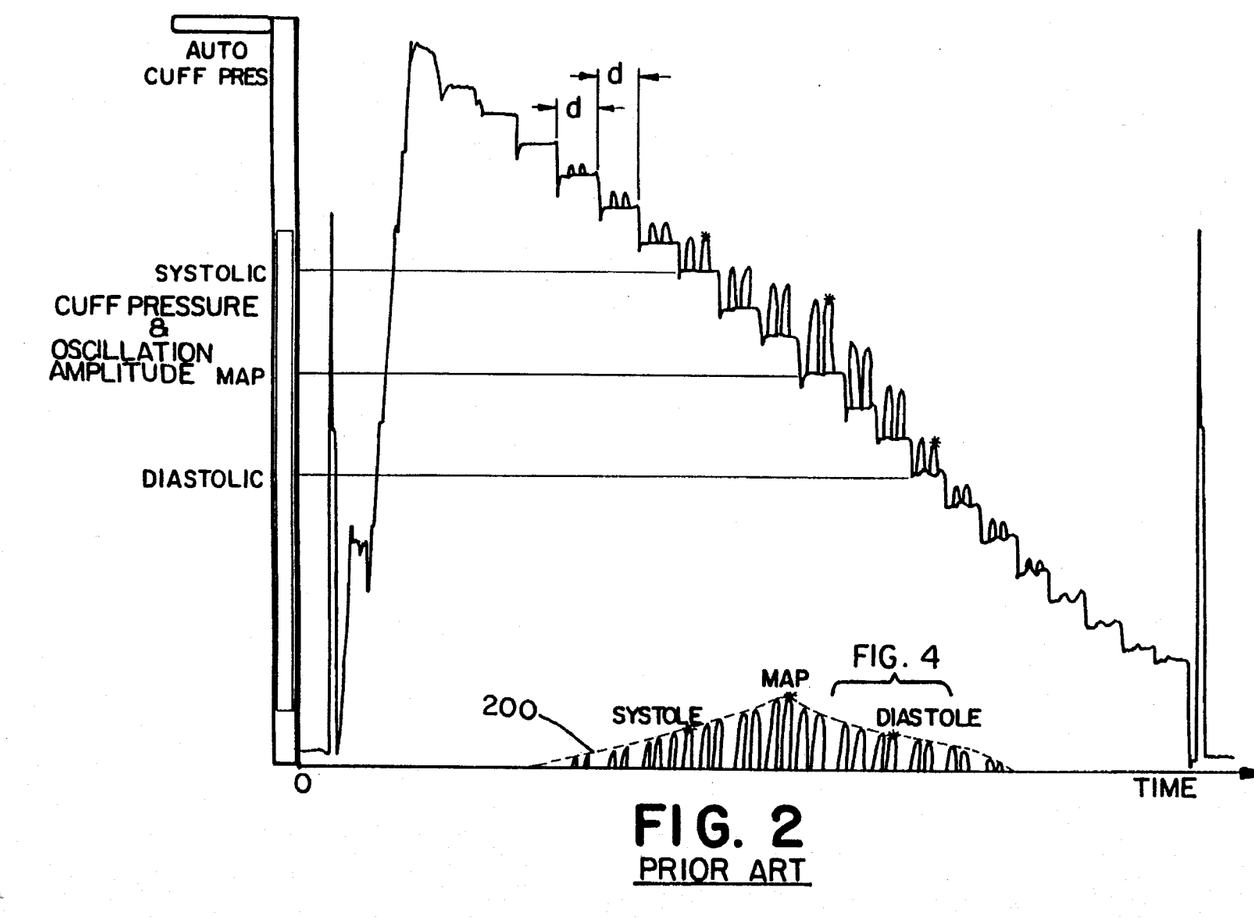
FIG. 2 is a pressure versus time graph illustrating a measuring cycle including step deflation steps and the corresponding oscillation complexes measured using a NIBP monitor in accordance with the invention.

In typical automatic sphygmomanometric devices, the cuff deflation operation is accomplished in equal decrements, usually about 8 mm Hg per step. Prior art FIG. 2 illustrates a pressure versus time graph illustrating a conventional cuff step deflation and measurement cycle for a conventional NIBP monitor. As illustrated, the cuff 101 is inflated to a pressure above the systolic pressure, and the cuff 101 is then deflated in steps of equal duration of about 8 mm Hg per step. A timeout duration d is provided at each step during which the signal processing circuitry searches for oscillation complexes in accordance with the techniques described in the afore-mentioned commonly assigned patents. At the end of timeout duration d, the cuff pressure is decremented even if no oscillation complex is detected. This process of decrementing the pressure and searching for oscillation complexes is repeated at least until MAP and/or the oscillometric envelope 200 may be determined. The entire blood pressure determination process is repeated at predetermined intervals, usually set by the user.

The operation of the "guard mode" technique in accordance with the invention will now be described with reference to the flow chart of FIG. 3. Those skilled in the art will appreciate that the flow chart of FIG. 3 is typically implemented in software on microprocessor 107 of FIG. 1 for controlling the triggering of the inflation/deflation and blood pressure measurement cycle.

As noted above, the idea behind a "guard mode" in accordance with the invention is to frequently inflate the cuff to a pressure below MAP and to compare the measured oscillometric signal to the corresponding "snapshot" signal stored for a similar pressure point on the oscillometric envelope during a previous blood pressure determination. If these signals differ by a predetermined amount, this indicates that the patient's blood pressure has changed significantly and should be measured immediately. For example, the "check inflate" to a pressure below MAP may run at a rate 5 times the cycle time selected for blood pressure measurements. The check inflate and related determination occur in addition to the normal determinations which occur at the predetermined measurement intervals.

Figure 3:
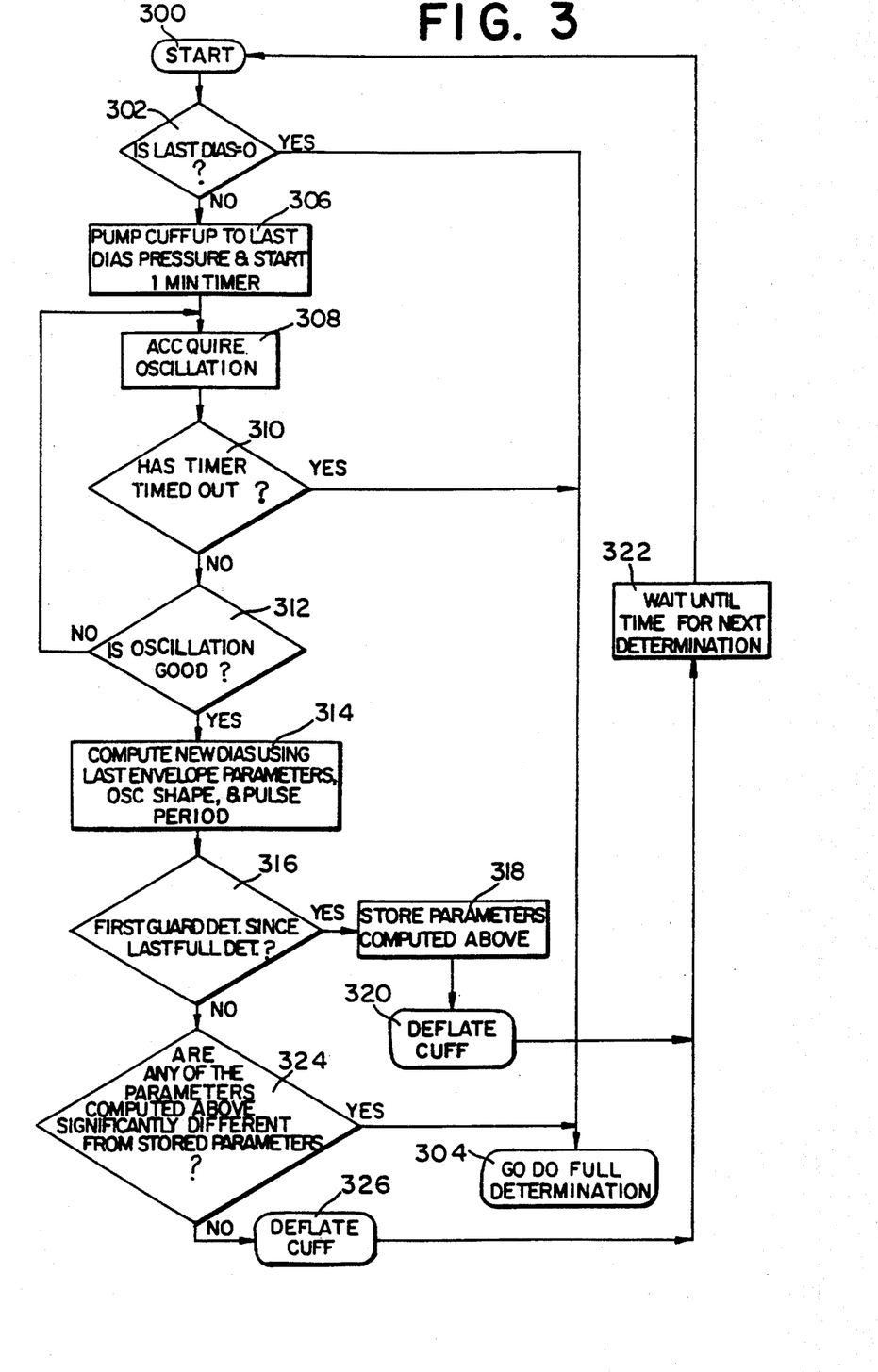
FIG. 3 is a flow chart representing the operation of the check inflate or "guard mode" under control of a microprocessor in accordance with the techniques of the invention.

As illustrated in FIG. 3, guard mode starts at step 300 and determines at step 302 whether there is an oscillometric envelope from an earlier blood pressure determination in parameter memory 108. In other words, it is determined whether a previous blood pressure determination has been conducted and whether parameters representing the diastolic pressure have been stored in parameter memory 108. If no previous blood pressure determination has been conducted, a full oscillometric blood pressure determination is conducted at step 304. Otherwise, cuff 101 is inflated at step 306 to the patient's last diastolic pressure, or some other pressure below MAP, for a "snapshot" or "guard mode" determination in accordance with the invention. A guard mode timer is also started at step 306 so that the overall guard mode determination will be completed in a sufficiently short amount of time (such as 1 minute) to minimize discomfort to the patient.

After the cuff 101 has been inflated at step 306, oscillation complexes are acquired using conventional techniques at step 308. Preferably, at least 4 oscillation complexes are measured. If it is determined at step 310 that the guard mode timer has timed out before the oscillation complexes have been gathered, a complete blood pressure determination is conducted at step 304. Otherwise, it is determined at step 312 whether each detected oscillation is of sufficient quality. Steps 308, 310 and 312 are repeated until the desired number of oscillations are acquired.

At step 314, a new diastolic pressure for the patient is computed using the measured envelope parameters. As noted above, these parameters include the shape of the diastolic part of the oscillation, oscillation amplitude at diastolic pressure, and pulse period. If it is determined at step 316 that this is the first guard mode determination (check inflate) after a complete blood pressure determination, more oscillations at higher pressures are measured and the stored parameters for the oscillation envelope are updated by storing the computed parameters for the oscillation envelope at step 318 and then deflating the cuff at step 320. This step is desired since conventional NIBP monitors typically do not collect the detailed parameter information during a normal NIBP determination which is desired in accordance with the invention. Microprocessor 107 then waits at step 322 until it is time for the next prescribed "guard mode" or complete blood pressure determination before starting the next guard mode determination. Of course, if such information is collected during a normal NIBP determination, steps 318 and 320 will be unnecessary.

If the present guard mode determination is not the first guard mode determination, the parameters from the oscillations at diastolic pressure computed at step 314 are compared at step 324 to the parameters saved from the first guard mode determination at step 318 after a normal blood pressure determination. If it is determined at step 324 that these parameters differ from each other by more than a predetermined amount, a full blood pressure determination is immediately conducted at step 304. However, if the parameters stored in parameter memory 108 at step 318 and the parameters currently computed at step 314 do not differ significantly, cuff 101 is deflated at step 326, and microprocessor 107 then waits at step 322 for the next guard mode determination or next full blood pressure determination.

As noted above, the parameters that are compared at step 324 include the oscillation amplitude, the shape of the diastolic part of the oscillation, and the pulse period. The comparison is preferably a percentage difference calculation which is defined as the absolute value of the current parameter C minus the stored parameter S times 100 divided by the stored parameter S (% Diff=|C-S|*100/S). Preferably, the current parameter C is the best average of at least four oscillations measured in the current check inflate cycle around diastolic and the stored parameter S is the best average of the at least four oscillations measured in the first guard mode (check inflate) after a complete determination for shape, the oscillometric envelope for amplitude, and the median period for the pulse.

In the presently preferred embodiment, a blood pressure determination is triggered at step 324 if the change in blood pressure is greater than 20 mm Hg, the change in oscillation amplitude or pulse period is 20% or more, or the change in the shape parameter is 10% or more. On the other hand, it may be desired to trigger a complete blood pressure determination if the sum of the percentage change in the shape parameter, the percentage change in oscillation amplitude and the percentage change in pulse period combined are greater than 30%. Of course, other thresholds may be set as desired to minimize the number of false positives and the number of false negatives.

The present inventors have discovered that the amplitude of the oscillometric signal is most sensitive to changes in blood pressure. However, if blood pressure rises enough to shift the entire oscillometric envelope such that a sample at the old diastolic level is now at about the systolic level, the measured amplitude may be similar to the stored amplitude. It is thus necessary to derive a technique for distinguishing oscillometric signals on the diastolic side of the oscillometric envelope from those on the systolic side of the oscillometric envelope. This is accomplished in accordance with the invention by introducing the afore-mentioned shape parameter for recording the shape of the diastolic phase of the oscillometric signal as the cuff pressure changes.

The shape parameter is introduced due to the significant change in oscillation shape between the systolic and diastolic pressures. In other words, the present inventors have quantified the shapes of the systolic and diastolic phases of the oscillometric envelope signal. In accordance with the invention, the shape computation is performed as follows, which is best understood with reference to FIG. 4, illustrating cuff pressure as a function of time.

Figure 4:
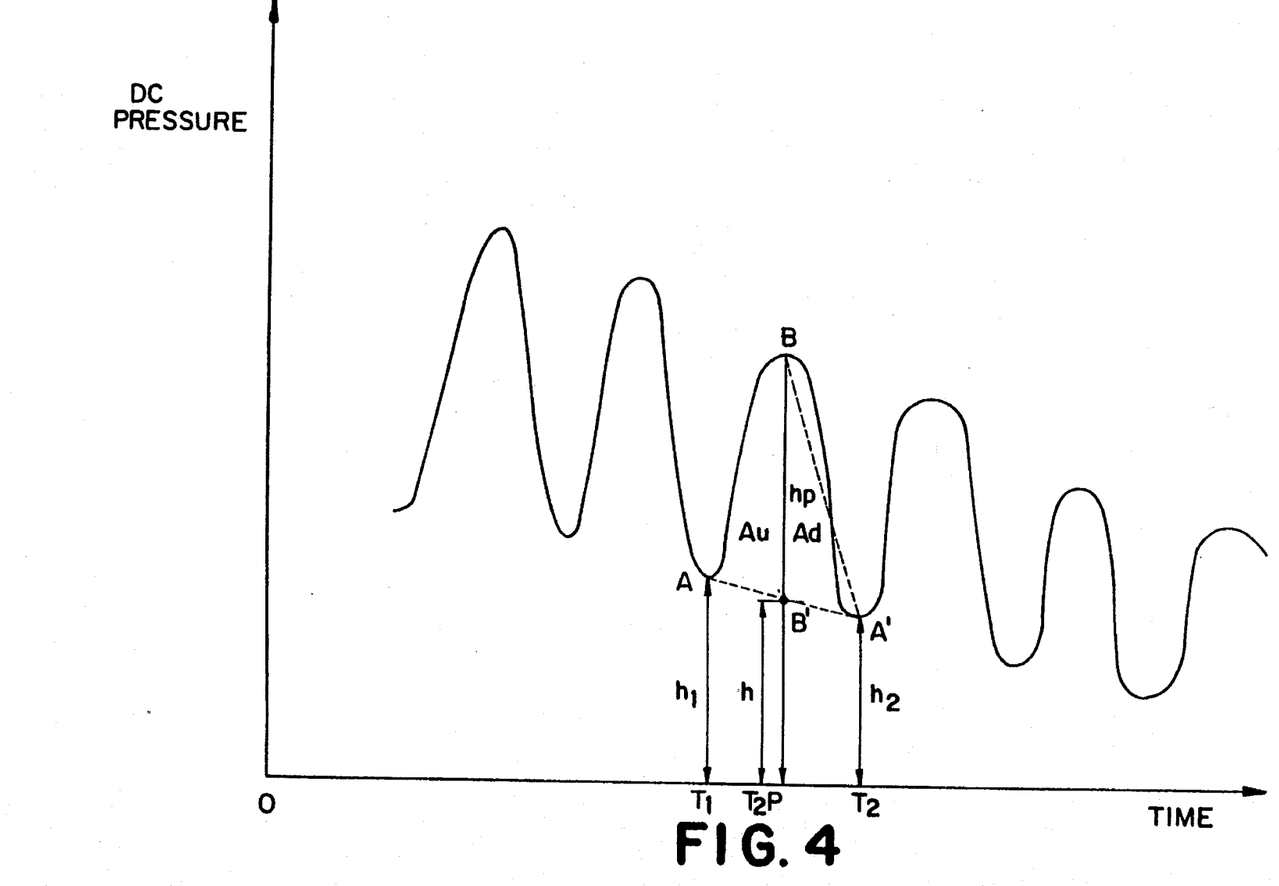
FIG. 4 is a pressure versus time graph illustrating a preferred technique for quantifying the shape of the oscillation complexes in accordance with the invention.

As shown in FIG. 4, an oscillation complex is divided into two parts, the part where the pressure is rising is the systolic phase and has an area $A_u$, while the part where the pressure is falling is the diastolic phase and has an area $A_d$. Areas $A_d$ and $A_d$ are calculated and stored. Then, the triangles that would fit the points at baseline and peak are computed. This is accomplished by drawing a line AA' from the start of one oscillation complex to the start of the next oscillation complex. Another line BB' is drawn perpendicular to the time axis from the peak $T_2P$ of the first oscillation complex to intersect the line AA' at B'. Yet another line BA' is drawn from the peak of the first oscillation complex to the start of the next oscillation complex. The line BA' completes a triangle that is on the diastolic phase of the oscillation complex. The area of triangle BB'A' is then divided into the area $A_d$ under the oscillation envelope that is between the peak of the first oscillation complex at point $T_2P$ and the start of the next oscillation complex at A' and above the line AA'. This ratio of the area of the oscillation, $A_d$, to the area of the triangle BB'A' is a measure of concavity and is stored as the afore-mentioned shape parameter. The present inventors have found experimentally that ratios for the diastolic part are less than one for oscillation complexes at cuff pressures greater than MAP (systolic phase of the oscillometric envelope) and greater than one for oscillation complexes at cuff pressures less than MAP (diastolic phase of the oscillometric envelope) and thus can be used to distinguish measurements on the diastolic and systolic sides of the oscillometric blood pressure envelope.

With reference again to FIG. 4, this procedure for calculating the ratio for discriminating oscillations on the diastolic phase of the oscillometric envelope from oscillations on the systolic phase of the oscillometric envelope may be described mathematically as follows:

$$h = \left( \frac{h_1 - h_2}{T_1 - T_2} \right)(T_2P - T_1) + h_1$$

$$Au = \left[ \sum_{i=T_1}^{T_2P} Y_i \right] - \frac{1}{2}(h_1 + h)(T_2P - T_1)$$

$$Ad = \left[ \sum_{i=T_2P}^{T_2} Y_i \right] - \frac{1}{2}(h + h_2)(T_2 - T_2P)$$

After substituting for h to eliminate the unknowns, the ratios ($A_{ur}$ and $A_{dr}$) may be taken as follows:

$$A_{ur} = \frac{A_u}{A_{ut}},$$

where $A_{ut}$ is the area of the triangle defined by points A, B and B'; and $$A_{dr} = \frac{A_d}{A_{dt}},$$

where $A_{dt}$ is the area of the triangle defined by points B, B' and A'.

By performing guard mode determinations in accordance with the invention in which it is necessary only to inflate to a pressure level below MAP and to maintain the pressure for only a few pulses, little trauma should be caused to the patient's limb as compared to a normal determination that must inflate higher than systolic pressure and slowly deflate to a level below diastolic pressure. A guard mode determination also allows users to select an interval which is much greater than that now used for monitoring a patient's blood pressure, thereby reducing the risk and discomfort to the patient. Preferably, the guard mode determination is completed quite quickly since it is only necessary to inflate to a relatively low pressure, such as diastolic pressure, search for a few (preferably 4) oscillation complexes, and then deflate the cuff completely. If there is no substantial change in the measured oscillometric pulse signal amplitudes, the determination is complete. On the other hand, if the oscillometric pulse signal amplitudes at the "snapshot" or check pressure have changed substantially, a complete blood pressure determination is initiated immediately.

It will be appreciated by those skilled in the art that the foregoing has set forth the presently preferred embodiment of the invention and an illustrative embodiment of the invention but that numerous alternative embodiments are possible without departing from the novel teachings of the invention. For example, those skilled in the art will appreciate that the techniques of the invention may be used for blood pressure monitors in which the pressure is incremented from diastolic pressure as described, for example, in U.S. Pat. No. 4,461,266 to Hood et al. Also, those skilled in the art will appreciate that the techniques of the invention may be used for blood pressure monitors which do not use the amplitude matching techniques described by Ramsey to determine whether oscillation complexes of sufficient quality have been received. In addition, those skilled in the art will appreciate that shape of the oscillation complexes may also be determined by accumulating the average of the second derivative from the peak of an oscillation complex to the end of the diastolic phase of the oscillation complex. Accordingly, all such modifications are intended to be included within the scope of the appended claims.

I claim:

1. An automated sphygmomanometer apparatus for determining a blood pressure of a patient, comprising:

an inflatable and deflatable pressure cuff;

inflating means operatively coupled to said cuff for selectively applying a medium under pressure to said cuff for inflating and pressurizing said cuff;

cuff pressure sensing means coupled to said cuff for sensing cuff pressure including any blood pressure oscillations therein;

deflating means operatively coupled to said cuff for selectively relieving pressure from said cuff;

memory means for storing first parameters representative of at least a predetermined point of an oscillometric envelope defined by blood pressure oscillations sensed during a blood pressure determination of said patient; and control means responsive to a cuff pressure determination of said cuff pressure sensing means for controlling said inflating means to inflate said cuff and said deflating means to deflate said cuff during respective blood pressure determinations of said patient at predetermined intervals and for storing in said memory means said first parameters during each blood pressure determination of said patient, said control means comprising means for initiating at least one check inflate cycle between respective blood pressure determinations by controlling said inflating means to inflate said cuff to a check pressure, means for acquiring blood pressure oscillations from said cuff pressure sensing means at said check pressure, means for computing second parameters from said blood pressure oscillations which are representative of a current blood pressure of said patient at said check pressure, and means for determining if said second parameters differ a predetermined amount from said first parameters and initiating a next blood pressure determination prior to the expiration of any of said predetermined intervals if said second parameters differ at least said predetermined amount from said first parameters.

2. An apparatus as in claim 1, wherein said predetermined point of said oscillometric envelope and said check pressure correspond to a diastolic pressure of the patient.

3. An apparatus as in claim 2, wherein said first and second parameters include diastolic pressure, oscillation shape at diastolic pressure, and a pulse period of said blood pressure oscillations.

4. An apparatus as in claim 1, wherein said means for initiating said check inflate cycle initiates respective check inflate cycles at intervals which are approximately ⅕ as long in duration as said predetermined interval.

5. An apparatus as in claim 1, further comprising means for discriminating blood pressure oscillations on a diastolic side of said oscillometric envelope from blood pressure oscillations on a systolic side of said oscillometric envelope.

6. An apparatus as in claim 5, wherein said discriminating means computes an area of a diastolic phase of a blood pressure oscillation and compares said area with an area of a triangle formed by a peak point of said blood pressure oscillation, an intersection point of a constant time line extending from said peak point to a baseline between respective blood pressure oscillations, and a beginning point on said baseline of a next blood pressure oscillation.

7. An apparatus as in claim 6, wherein said discriminating means determines a blood pressure oscillation to be on said diastolic side of said oscillometric envelope when a ratio of said area of said diastolic phase of said blood pressure oscillation to said area of said triangle is equal to at least approximately 1, and determines said blood pressure oscillation to be on said systolic side of said oscillometric envelope when said ratio of said area of said diastolic phase of said blood pressure oscillation to said area of said triangle is equal to less than approximately 1.

8. An automatic oscillometric blood pressure monitor comprising:

a pressurized cuff;

means for inflating and deflating said cuff;

means for measuring arterial pressure oscillation complexes through measurement of time varying pressures within said cuff;

means for determining the patient's blood pressure at predetermined intervals by instructing said inflating and deflating means to inflate said cuff about an artery of a patient until said cuff is at a pressure level above the patient's estimated systolic pressure and to deflate said cuff by predetermined pressure decrements, by searching for arterial pressure oscillation complexes at each pressure level, and by determining, from said arterial pressure oscillation complexes, first parameters representative of at least a portion of an oscillometric envelope of the patient;

means for monitoring a patient's blood pressure between blood pressure determinations by said blood pressure determining means by controlling said inflating means to inflate said cuff about an artery of the patient until said cuff is at a check pressure level at said portion of said oscillometric envelope of the patient, by searching for oscillation complexes at said check pressure level, and by determining, from oscillation complexes detected at said check pressure level, second parameters which are representative of a current blood pressure of the patient at said check pressure level; and means responsive to said blood pressure monitoring means for determining if said second parameters differ a predetermined amount from said first parameters and for immediately initiating a blood pressure determination by said blood pressure determining means prior to the expiration of any of said predetermined intervals if said second parameters differ said predetermined amount from said first parameters.

9. A method of monitoring a patient's blood pressure, comprising the steps of:

determining, at predetermined intervals, the patient's blood pressure using an oscillometric blood pressure monitor;

storing first parameters representative of at least a portion of an oscillometric envelope of the patient during respective blood pressure determinations;

checking for changes in the patient's blood pressure between respective blood pressure determinations by performing the steps of:

inflating a blood pressure cuff to a check pressure, searching for arterial pressure oscillation complexes at said check pressure, computing second parameters representative of at least said portion of a current oscillometric envelope of the patient from oscillation complexes which are representative of a blood pressure of the patient at at least said portion of the current oscillometric envelope of the patient; and initiating a blood pressure determination by said oscillometric blood pressure monitor prior to the expiration of any of said predetermined intervals if said second parameters differ a predetermined amount from said first parameters.

10. A method as in claim 9, wherein said portion of said oscillometric envelope and said check pressure correspond to diastolic pressure.

11. A method as in claim 10, wherein said first and second parameters include diastolic pressure, oscillation shape at diastolic pressure, and a pulse period of said oscillation complexes.

12. A method as in claim 9, comprising the further step of repeating said checking step at intervals which are approximately ⅕ as long in duration as said predetermined intervals.

13. A method as in claim 9, wherein said checking step comprises the further step of discriminating blood pressure oscillation complexes on a diastolic side of the current oscillometric envelope from blood pressure oscillation complexes on a systolic side of the current oscillometric envelope.

14. A method as in claim 13, wherein said discriminating step comprises the further steps of computing an area of a diastolic phase of a blood pressure oscillation complex and calculating a ratio of said area with an area of a triangle formed by a peak point of said blood pressure oscillation complex, an intersection point of a constant time line from said peak point to a baseline between respective blood pressure oscillation complexes, and a beginning point on said baseline of a next blood pressure oscillation complex.

15. A method as in claim 14, wherein said discriminating step comprises the further step of determining a blood pressure oscillation complex to be on said diastolic side of the current oscillometric envelope when said ratio of said area of said diastolic phase of said blood pressure oscillation complex to said area of said triangle is equal to at least approximately 1, and determining said blood pressure oscillation complex to be on said systolic side of the current oscillometric envelope when said ratio of said area of said diastolic phase of said blood pressure oscillation complex to said area of said triangle is equal to less than approximately 1.

16. A method of monitoring a patient's blood pressure using an automatic oscillometric blood pressure monitor comprising a pressurized cuff, means for inflating and deflating said cuff, means for measuring arterial pressure oscillation complexes through measurement of time varying pressures within said cuff, and means for determining a patient's blood pressure at predetermined intervals by instructing said inflating and deflating means to inflate said cuff about an artery of the patient until said cuff is at a pressure level above the patient's estimated systolic pressure and to deflate said cuff by predetermined pressure decrements, by searching for arterial pressure oscillation complexes at each pressure levels and by determining, from said arterial pressure oscillation complexes, first parameters representative of at least a portion of an oscillometric envelope of the patient, said method of monitoring the patient's blood pressure comprising the steps of:

initiating at least one check inflate cycle between respective blood pressure determinations at said predetermined intervals by controlling said inflating means to inflate said cuff to a check pressure;

acquiring blood pressure oscillation complexes from said cuff pressure sensing means at said check pressure;

computing second parameters from said blood pressure oscillation complexes which are representative of a blood pressure of the patient at said check pressure;

determining if said second parameters representative of the blood pressure of the patient at said check pressure differ a predetermined amount from said first parameters; and if said second parameters differ said predetermined amount from said first parameters, immediately initiating a blood pressure determination prior to the expiration of said predetermined interval.

17. A method as in claim 16, wherein said portion of the oscillometric envelope of the patient is around diastolic pressure for the patient, and said check pressure is approximately equal to the patient's diastolic pressure.

* * * * *

UNITED STATES PATENT AND TRADEMARK OFFICE
CERTIFICATE OF CORRECTION

PATENT NO. : 5,606,977
DATED : March 4, 1997
INVENTOR(S) : Maynard Ramesey III and Richard Medero It is certified that error appears in the above-indentified patent and that said Letters Patent is hereby corrected as shown below:

Column 7, line 52, change "$A_d$" to --$A_u$--.

Signed and Sealed this

Fifteenth Day of July, 1997

Attest:

Attesting Officer

BRUCE LEHMAN

*Commissioner of Patents and Trademarks*